(12) United States Patent
Talyansky et al.

(10) Patent No.: US 9,097,670 B1
(45) Date of Patent: Aug. 4, 2015

(54) SYSTEM FOR MEASURING DYE CONCENTRATION IN LIQUIDS

(71) Applicants: Vitaly Talyansky, Portland, OR (US); Edward Talyansky, Battle Ground, WA (US)

(72) Inventors: Vitaly Talyansky, Portland, OR (US); Edward Talyansky, Battle Ground, WA (US)

(73) Assignee: Stardust Materials, LLC, Vancouver, WA (US)

( * ) Notice: Subject to any disclaimer, the term of this patent is extended or adjusted under 35 U.S.C. 154(b) by 0 days.

(21) Appl. No.: 14/199,201

(22) Filed: Mar. 6, 2014

(51) Int. Cl.
*G01N 21/64* (2006.01)

(52) U.S. Cl.
CPC ...... *G01N 21/645* (2013.01); *G01N 2021/6482* (2013.01); *G01N 2021/6491* (2013.01)

(58) Field of Classification Search
USPC .................................................... 250/432 R
See application file for complete search history.

(56) References Cited

U.S. PATENT DOCUMENTS

| 4,262,206 | A | * | 4/1981 | Viehmann ................. 250/483.1 |
| 4,981,779 | A | * | 1/1991 | Wagner ..................... 435/287.9 |
| 5,747,349 | A | * | 5/1998 | van den Engh et al. ...... 436/172 |
| 6,531,097 | B1 | * | 3/2003 | Vojnovic et al. ........... 422/82.07 |
| 6,680,211 | B2 | * | 1/2004 | Barbera-Guillem et al. . 436/533 |

* cited by examiner

*Primary Examiner* — Phillip A Johnston

(57) ABSTRACT

Apparatus and methods for measuring dye concentration in liquids are described herein. An example method includes emitting first electromagnetic radiation having a first wavelength through a first end of a tube for a first duration of time, the tube being filled with a liquid and a dye diluted in the liquid to a first concentration, ceasing the emission of the first electromagnetic radiation for a second duration of time following the first duration of time, detecting a first strength of second electromagnetic radiation emitted by a luminophor coated on a screen at a second end of the tube at the conclusion of the second duration of time, the luminophor having luminescent properties such that the first electromagnetic radiation causes the luminophor to emit the second electromagnetic radiation having a second wavelength, wherein the second electromagnetic radiation is partially absorbed by the dye and the amount of the second electromagnetic radiation absorbed by the dye depends on the first concentration, and determining the first concentration based on the first strength.

20 Claims, 5 Drawing Sheets

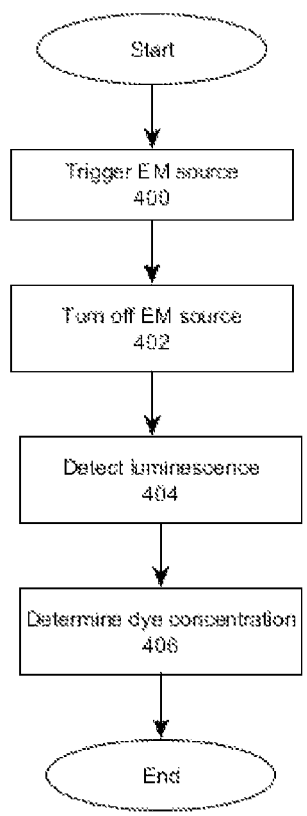

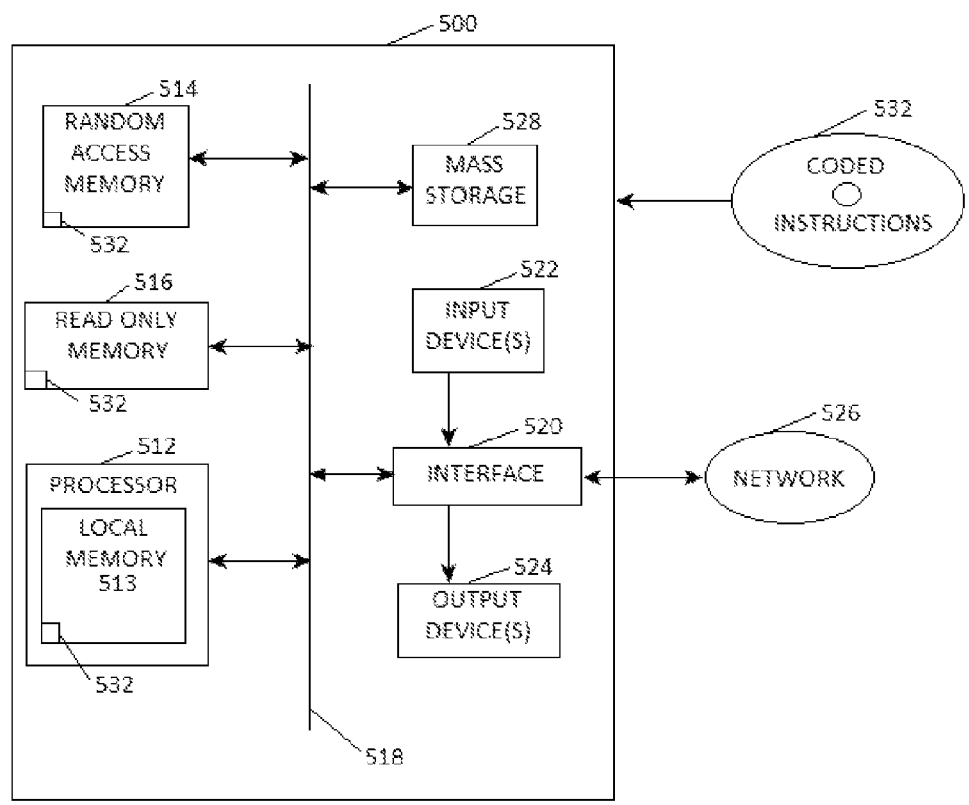

SYSTEM FOR MEASURING DYE CONCENTRATION IN LIQUIDS

FIELD OF THE DISCLOSURE

The present disclosure relates generally to identifying and/or authenticating liquids and, more particularly, to a system for measuring dye concentration in liquids.

BACKGROUND

A liquid can be marked for identification by dissolving a dye in the liquid to a certain concentration. The concentration of the dye in the liquid can later be measured and compared to the expected concentration to identify the liquid.

BRIEF DESCRIPTION OF THE DRAWINGS

FIG. 4 is a flowchart representative of example machine readable instructions that may be executed to implement the example system of FIG. 1.

FIG. 5 is a block diagram of an example processing system capable of executing the example machine readable instructions of FIGS. 2-4 to implement the example system of FIG. 1.

DETAILED DESCRIPTION

Figure 1:
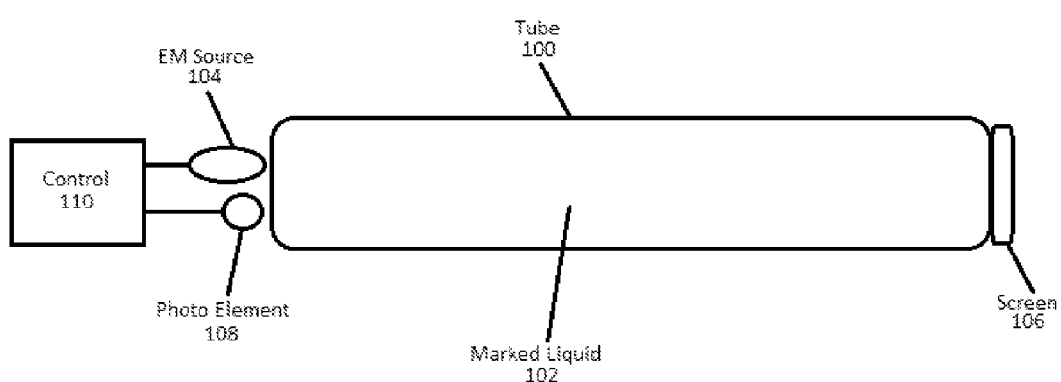
FIG. 1 is a block diagram of a system for measuring dye concentration in liquids constructed in accordance with the teachings of this disclosure.

Dyes can be used to mark liquids for future identification and/or authentication. By dissolving a dye in a liquid to a known concentration, the liquid can later be identified by detecting the concentration of the dye in the liquid. If the dye is detected in the appropriate known concentration, then the liquid can be identified as authentic. If the dye is not detected or if the dye is detected in the wrong concentration, then the liquid can be identified as not being the marked liquid. This identification of liquids is useful to avoid misidentifying a liquid and/or detecting counterfeit or adulterated liquids.

One method of detecting a marked liquid in which a dye has been dissolved is to measure the light absorption of the marked liquid when it is illuminated by light of a certain wavelength. One type of dye that could be used for this purpose would be an organic dye soluble in solvents that has a high optical density. A dye with sufficient optical density can be used to identify a liquid in this manner when the dye is dissolved in a liquid to a concentration as small as 50-100 parts per billion.

Some organic dyes luminesce when illuminated by light with a particular wavelength. Luminescence is a response of certain optical materials to electromagnetic radiation. More specifically, a luminescent material that is illuminated and excited with electromagnetic radiation at a certain wavelength will emit electromagnetic radiation in response at a different wavelength. The difference between the wavelengths of the electromagnetic radiation that excites the material and the electromagnetic radiation produced in response to this illumination is known as the Stokes shift. It is theoretically possible to measure the concentration of such a dye in a marked liquid by measuring the strength of the luminescence of the dye. However, the wavelength of the luminescent signal is typically close to the wavelength of the signal needed to illuminate and excite the dye to create the luminescence (i.e., the Stokes shift is small). Furthermore, the decay time of the luminescent signal (i.e., the time that the luminescence continues to be emitted after the illuminating signal is removed) is quite short; typically around 3-15 nanoseconds. Because of this short decay time, the luminescence of the dye would have to be measured while the illuminating signal is present. However, because of the small Stokes shift, it is difficult to distinguish between the illuminating signal and the luminescent signal. Thus, it is difficult to accurately measure the concentration of an organic dye in a marked liquid in this manner.

In contrast to the short decay times of organic dyes, inorganic ceramic luminophors luminesce with much longer decay times, typically ranging from 0.05-10 milliseconds. This allows the luminescent signal of a ceramic luminophor to be measured after the signal illuminating and exciting the luminophors is turned off, thus allowing the luminescence to be measured without any interference from the illuminating signal. However, ceramic luminophors are insoluble in most solvents and in water and they are often not desirable in consumer products such as fuel, pharmaceuticals and beverages. The present disclosure combines the benefits of organic dyes and ceramic luminophors in a system to mark and identify and/or authenticate liquids.

Example methods, apparatus, and/or articles of manufacture disclosed herein provide a system for measuring dye concentration in liquids. In examples disclosed herein, a liquid that is transparent over a certain spectral range is marked by diluting an organic dye with luminescent properties in the liquid. In examples disclosed herein, the marked liquid is placed in a tube that is transparent on each of its ends. In examples disclosed herein, an excitation source at one end of the tube emits light through the tube and through the marked liquid in the tube. In examples disclosed herein, the other end of the tube has a screen coated with a ceramic luminophor that luminesces when it is illuminated by the excitation source. In examples disclosed herein, the luminescence of the screen coated with the ceramic luminophor causes light to travel back through the marked liquid in the tube. In examples disclosed herein, this luminescent signal is partially absorbed by the dye in the liquid, with the amount of absorption dependent on the concentration of the dissolved dye. In examples disclosed herein, a photo element at the first end of the tube measures the luminescence produced by the ceramic luminophor that is not absorbed by the dye in the marked liquid. In examples disclosed herein, the concentration of the dye in the marked liquid is determined based on the strength of the luminescence measured by the photo element.

FIG. 1 is a block diagram of an example system for measuring dye concentration in liquids constructed in accordance with the teachings of this disclosure. The example of FIG. 1 includes a tube 100, a marked liquid 102, an EM source 104, a screen 106, a photo element 108 and a control 110.

In the illustrated example, the tube 100 is a glass tube whose ends are transparent over a certain spectral range between wavelengths L1 and L2. In other examples, the tube 100 may be constructed of any other material so long as the ends of the tube are transparent over the appropriate range of wavelengths.

In the illustrated example, the marked liquid 102 is a liquid to be identified and/or authenticated (e.g., fuel) in which an organic dye has been diluted to a certain concentration. The example marked liquid 102 is at least somewhat transparent between the wavelengths L1 and L2. In the illustrated example, the organic dye is invisible to the naked eye and is thus used as a covert security feature. In other examples, the organic dye is visible to the naked eye and is used as an overt security feature. In some examples, the organic dye luminesces when illuminated by visible light. In some examples, the organic dye luminesces when illuminated by infrared light. In other examples, the organic dye luminesces when illuminated by ultra-violet light.

In the illustrated example, the EM source 104 emits electromagnetic radiation through the tube 100 and through the marked liquid 102 in the tube 100. In the illustrated example, the EM source 104 emits light of wavelength L3, where the wavelength L3 is between the wavelengths L1 and L2 and the wavelength L3 is weakly absorbed by the marked liquid 102. The example EM source 104 may emit visible light, infrared light, ultra-violet light or radiation from any other part of the electromagnetic spectrum. In the illustrated example, the EM source 104 is an LED. In other examples, the EM source 104 may be a laser or any other device capable of emitting electromagnetic radiation of the appropriate wavelength L3. In some examples, the EM source 104 consists of multiple LEDs, multiple lasers or other multiple sources of electromagnetic radiation.

In the illustrated example, the screen 106 is visible through the ends of the tube 100. The example screen 106 is coated with a ceramic luminophor that has a thickness of at least 20 microns. The ceramic luminophor on the example screen 106 is excited by the light with wavelength L3 emitted by the example EM source 104. When the luminophor on the example screen 106 is excited by this emitted light, the luminophor emits luminescence in a narrow spectral range with a peak wavelength L4. The luminescence of the luminophor on the example screen 106 with wavelength L4 is actively absorbed by the dye in the example marked liquid 102. The ceramic luminophor on the example screen 106 has a relatively long decay time, such that it continues to luminesce for about 0.05 to 10 milliseconds after the example EM source 104 is turned off (i.e., the luminophor has an afterglow).

In the illustrated example, the photo element 108 measures the luminescence of the luminophor on the example screen 106. In the illustrated example, the photo element 108 is a photodiode. In other examples, the photo element 108 may be any other device capable of measuring the luminescence of the luminophor on the example screen 106.

In the illustrated example, the control 110 communicates with and controls the EM source 104 and the photo element 108. The example control 110 sends information to the EM source 104 and the photo element 108 and receives information from the photo element 108.

While an example manner of implementing the system for measuring dye concentration in liquids has been illustrated in FIG. 1, one or more of the elements, processes and/or devices illustrated in FIG. 1 may be combined, divided, re-arranged, omitted, eliminated and/or implemented in any other way. Further, the example tube 100, the example marked liquid 102, the example EM source 104, the example screen 106, the example photo element 108, the example control 110 and/or, more generally, the example system for measuring dye concentration in liquids of FIG. 1 may be implemented by hardware, software, firmware and/or any combination of hardware, software and/or firmware. Thus, for example, any of the example tube 100, the example marked liquid 102, the example EM source 104, the example screen 106, the example photo element 108, the example control 110 and/or, more generally, the example system for measuring dye concentration in liquids of FIG. 1 could be implemented by one or more circuit(s), programmable processor(s), application specific integrated circuit(s) (ASIC(s)), programmable logic device(s) (PLD(s)), microprocessor(s), hardware processor(s), and/or field programmable logic device(s) (FPLD(s)), etc. When any of the system or apparatus claims of this patent are read to cover a purely software and/or firmware implementation, at least one of the example tube 100, the example marked liquid 102, the example EM source 104, the example screen 106, the example photo element 108, the example control 110 and/or, more generally, the example system for measuring dye concentration in liquids of FIG. 1 is hereby expressly defined to include a tangible computer readable storage medium such as a memory, DVD, CD, Blu-ray, etc. storing the software and/or firmware. Further still, the example tube 100, the example marked liquid 102, the example EM source 104, the example screen 106, the example photo element 108, the example control 110 and/or, more generally, the example system for measuring dye concentration in liquids of FIG. 1 may include more than one of any or all of the illustrated elements, processes and devices.

Figure 2:
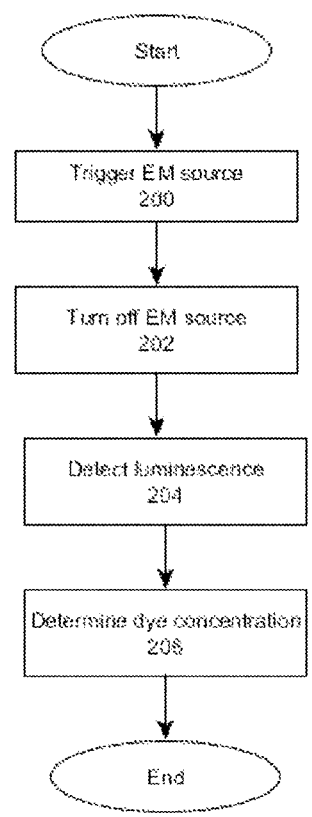
FIG. 2 is a flowchart representative of example machine readable instructions that may be executed to implement the example system of FIG. 1.
Figure 3:
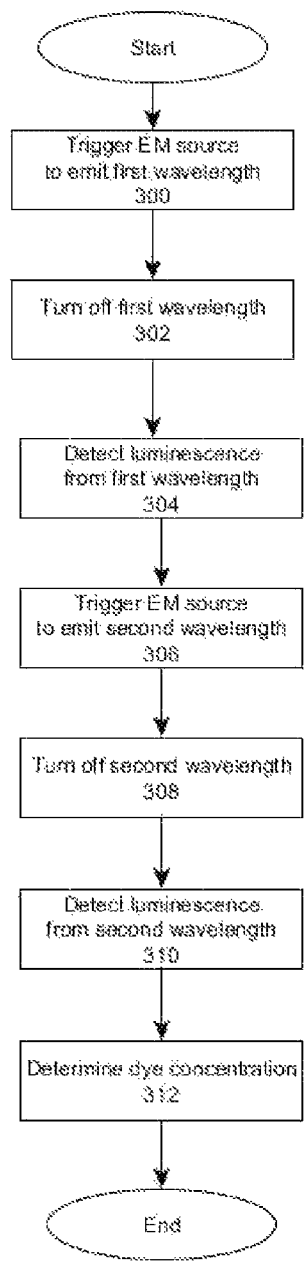
FIG. 3 is a flowchart representative of example machine readable instructions that may be executed to implement the example system of FIG. 1.

FIGS. 2-4 are flowcharts representative of example machine readable instructions for implementing the example system for measuring dye concentration in liquids of FIG. 1. In the example flowcharts of FIGS. 2-4, the machine readable instructions comprise program(s) for execution by a processor such as the processor 512 shown in the example computer 500 discussed below in connection with FIG. 5. The program(s) may be embodied in software stored on a tangible computer readable storage medium such as a CD-ROM, a floppy disk, a flash drive, a hard drive, a digital versatile disk (DVD), a Blu-ray disk, or a memory associated with the processor 512, but the entire program and/or parts thereof could alternatively be executed by a device other than the processor 512 and/or embodied in firmware or dedicated hardware. Further, although the example program(s) is described with reference to the flowcharts illustrated in FIGS. 2-4, many other methods of implementing the example system for measuring dye concentration in liquids of FIG. 1 may alternatively be used. For example, the order of execution of the blocks may be changed, and/or some of the blocks described may be changed, eliminated, or combined.

As mentioned above, the example processes of FIGS. 2-4 may be implemented using coded instructions (e.g., computer readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage media in which information is stored for any duration (e.g., for extended time periods, permanently, brief instances, for temporarily buffering, and/or for caching of the information). As used herein, the term tangible computer readable storage medium is expressly defined to include any type of computer readable storage device and/or disk and to exclude propagating signals. Additionally or alternatively, the example processes of FIGS. 2-4 may be implemented using coded instructions (e.g., computer readable instructions) stored on a non-transitory computer readable medium such as a hard disk drive, a flash memory, a read-only memory, a compact disk, a digital versatile disk, a cache, a random-access memory and/or any other storage media in which information is stored for any duration (e.g., for extended time periods, permanently, brief instances, for temporarily buffering, and/or for caching of the information). As used herein, the term non-transitory computer readable storage medium is expressly defined to include any type of computer readable storage device and/or disk and to exclude propagating signals. As used herein, when the phrase "at least" is used as the transition term in a preamble of a claim, it is open-ended in the same manner as the term "comprising" is open ended. Thus, a claim using "at least" as the transition term in its preamble may include elements in addition to those expressly recited in the claim.

FIG. 2 begins when the example control 110 triggers the example EM source 104 (block 200). This causes the example EM source 104 to emit light through the example tube 100 and through the example marked liquid 102 in the tube 100. In the illustrated example, the EM source 104 emits visible light with a wavelength L3. In other examples, the EM source 104 may emit infrared light, ultraviolet light or any other type of electromagnetic radiation. The light emitted by the example EM source 104 causes the ceramic luminophor on the example screen 106 to luminesce and emit light with a wavelength L4. In the illustrated example, the dye in the marked liquid 102 also luminesces and emits light with a wavelength relatively close to L4.

After the example control 110 triggers the EM source 104 (block 200), the control 110 turns off the EM source 104 (block 202) a short time later (e.g., 5 milliseconds). The example control 110 keeps the example EM source 104 emitting light long enough for the luminophor on the example screen 106 to luminesce with a significantly strong signal to be detected by the example photo element 108. After the example control 110 turns off the example EM source 104 (block 202), the luminescence of both the dye in the example marked liquid 102 and the luminophor on the example screen 106 begins to decrease in signal strength. However, these luminescent emissions do not end immediately after the example EM source 104 is turned off. Instead, the luminescent emissions continue to luminesce for a short period of time after the example EM source 104 is turned off (i.e., there is an afterglow). In the illustrated example, the afterglow of the organic dye in the marked liquid 102 lasts about 3-15 nanoseconds. However, the afterglow of the ceramic luminophor on the example screen 106 lasts about 0.05-10 milliseconds.

After the example control 110 turns off the example EM source 104 (block 202), the control 110 measures the signal detected by the example photo element 108 after a short pause (block 204). The pause between when the example control 110 turns off the example EM source 104 (block 202) and when the control 110 measures the signal detected by the example photo element 108 (block 204) is long enough for the afterglow of the luminescence of the dye in the example marked liquid 102 to significantly decay but short enough that the afterglow of the luminescence of the luminophor on the screen 106 is still sufficiently present to be detected by the example photo element 108. This pause is typically 1-5 milliseconds but could be longer or shorter depending on the decay times of the luminescence of the dye in the example marked liquid 102 and the luminophor on the example screen 106. Because of this pause, when the example control 110 measures the signal detected by the example photo element 108 (block 204), the only signal detected by the photo element 108 and measured by the control 110 is the luminescence of the luminophor on the example screen 106.

After the example control 110 measures the signal detected by the example photo element 108 (block 204), the control 110 determines the dye concentration in the example marked liquid 102 based on this measured signal. Because the dye in the example marked liquid 102 actively absorbs the luminescence emitted by the luminophor on the example screen 106, only the portion of this luminescence unabsorbed by the dye will be detected by the example photo element 108. Therefore, after an appropriate calibration, the example control 110 can determine the dye concentration in the example marked liquid 102 from the signal detected by the example photo element 108. For example, a calibration of the system may include measuring the signal detected by the example photo element 108 with no dye in the example marked liquid 102 and then measuring the signal detected by the photo element 108 with a dye diluted in the marked liquid 102 to a known concentration. Using these two measurements, a linear relationship between the concentration of the dye in the example marked liquid 102 and the signal detected by the example photo element 108 can be determined. The example control 110 can then use this linear relationship to determine the concentration of dye in the example marked liquid 102 for any measured signal detected by the example photo element 108. After the example control 110 determines the dye concentration in the example marked liquid 108 (block 206), the example of FIG. 2 ends.

FIG. 3 is a flowchart representative of alternative example machine readable instructions for implementing the example system for measuring dye concentration in liquids of FIG. 1. In the example of FIG. 3, the EM source 104 of FIG. 1 emits electromagnetic radiation having two different wavelengths through the example tube 100. In the illustrated example of FIG. 3, the EM source 104 consists of two LEDs in parallel that emit light at two different wavelengths. In some examples, the EM source 104 may consist of two laser diodes, or one LED and one laser diode or any combination of two devices capable of emitting electromagnetic radiation at two different wavelengths. In other examples, the EM source 104 is a single device capable of emitting two different wavelengths of electromagnetic radiation at different times. In the illustrated example of FIG. 3, the two emissions of light at different wavelengths each cause the luminophor on the screen 106 to luminesce. One of the wavelengths of light emitted by the example EM source 104 causes the example screen 106 to emit luminescence that is strongly absorbed by the dye in the example marked liquid 102. The other wavelength of light emitted by the example EM source 104 causes the example screen 106 to emit luminescence that is either not absorbed at all or is weakly absorbed by the dye in the example marked liquid 102.

FIG. 3 begins when the example control 110 triggers the example EM source 104 to emit light with wavelength L5 through the example tube 100 and through the example marked liquid 102 (block 300). This emission of light with wavelength L5 excites the luminophor on the example screen 106 and causes it to luminesce and emit light with a peak wavelength L6. This luminescence of light with wavelength L6 is actively absorbed by the dye in the example marked liquid 102. The emission of light with wavelength L5 by the example EM source 104 may also cause luminescence by the dye in the example marked liquid 102.

A short time after the example control 110 triggers the example EM source 104 to emit light with wavelength L5 (block 300), the control 110 turns off the emission of light with wavelength L5 by the EM source 104 (block 302). The example EM source 104 emits light with wavelength L5 long enough for the luminophor on the example screen 106 to luminesce at or near its peak strength. After the example EM source 104 stops emitting light with wavelength L5, the luminescent emissions of both the dye in the example marked liquid 102 and the luminophor on the example screen 106 continue for a short time as an afterglow but begin to decay quickly. The afterglow of the luminescence of the dye in the example marked liquid 102 lasts about 3-15 nanoseconds and the afterglow of the luminescence of the luminophor on the example screen 106 lasts about 0.05-10 milliseconds.

A short time after the example control 110 turns off the emission of light with wavelength L5 by the example EM source 104 (block 302), the control 110 measures the luminescence detected by the example photo element 108 (block 304). The example control 110 pauses between turning off the emission by the example EM source 104 (block 302) and measuring the luminescence detected by the example photo element 108 (block 304). The length of this pause is long enough such that the afterglow of the luminescence by the dye in the example marked liquid 102 has decayed enough such that it cannot be detected by the example photo element 108 but short enough that the afterglow of the luminescence by the luminophor on the example screen 106 can still be detected by the photo element 108 (e.g., 1-5 ms). Therefore, after this pause, the only emission detected by the example photo element 108 will be from the luminescence of the luminophor on the example screen 106.

After the example control 110 measures the luminescence of the luminophor on the example screen 106 (block 304), the control 110 triggers the example EM source 104 to emit light with a wavelength L7 through the example tube 100 and through the example marked liquid 102 (block 306). This emission of light with wavelength L7 excites the luminophor on the example screen 106 and causes it to luminesce and emit light with a peak wavelength L8. This luminescence of light with wavelength L8 is not absorbed by the dye in the example marked liquid 102. Thus, the emission of light with wavelength L8 by the example EM source 104 causes little or no luminescence by the dye in the example marked liquid 102.

A short time after the example control 110 triggers the example EM source 104 to emit light with wavelength L7 (block 306), the control 110 turns off the emission of light with wavelength L7 by the EM source 104 (block 308). The example EM source 104 emits light with wavelength L7 long enough for the luminophor on the example screen 106 to luminesce at or near its peak strength. After the example EM source 104 stops emitting light with wavelength L7, the luminescent emission of the luminophor on the example screen 106 and any luminescence by the dye in the example marked liquid 102 continue for a short time as an afterglow but begin to decay quickly. The afterglow of any luminescence of the dye in the example marked liquid 102 lasts about 3-15 nanoseconds and the afterglow of the luminescence of the luminophor on the example screen 106 lasts about 0.05-10 milliseconds.

A short time after the example control 110 turns off the emission of light with wavelength L7 by the example EM source 104 (block 308), the control 110 measures the luminescence detected by the example photo element 108 (block 310). The example control 110 pauses between turning off the emission by the example EM source 104 (block 308) and measuring the luminescence detected by the example photo element 108 (block 310). The length of this pause is long enough such that the afterglow of any luminescence by the dye in the example marked liquid 102 has decayed enough such that it cannot be detected by the example photo element 108 but short enough that the afterglow of the luminescence by the luminophor on the example screen 106 can still be detected by the photo element 108 (e.g., 1-5 milliseconds). Therefore, after this pause, the only emission detected by the example photo element 108 will be from the luminescence of the luminophor on the example screen 106.

After the example control 110 measures the luminescence detected by the example photo element 108 (block 310), the control 110 determines the dye concentration in the example marked liquid 102 (block 312). The example control 110 determines the dye concentration in the example marked liquid 102 (block 312) by comparing the ratio of the strength of the luminescence detected by the example photo element 108 in response to the emission of light with the first wavelength L5 to the strength of the luminescence detected by the example photo element 108 in response to the emission of light with the second wavelength L7. The luminescence emitted by the luminophor on the example screen 106 in response to the light with wavelength L5 emitted by the example EM source 104 will be partially absorbed by the dye in the example marked liquid 102. The amount of the absorption will depend on the concentration of the dye in the marked liquid 102. Thus, the larger the dye concentration in the example marked liquid 102, the smaller the detected luminescence will be in block 304. However, the luminescence emitted by the luminophor on the example screen 106 in response to the light with wavelength L7 emitted by the example EM source 104 will not be absorbed by the dye in the example marked liquid 102. Thus, the luminescence detected in block 310 will be the same regardless of the dye concentration in the example marked liquid 102. Therefore, the ratio of the luminescence measured in block 304 to the luminescence measured in block 310 will be inversely proportional to the concentration of the dye in the marked liquid 102. After an appropriate calibration, the example control 110 determines the dye concentration in the example marked liquid 102 based on this ratio (block 312). For example, a calibration may be performed by measuring the luminescence detected by the photo element 108 in response to each of the two emissions of light with different wavelengths emitted by the example EM source 104 when the example marked liquid 102 contains no dye and when a dye is diluted in the example marked liquid 102 to a known concentration. After the example control 110 determines the dye concentration in the example marked liquid 102 (block 312), the example of FIG. 3 ends.

FIG. 4 is a flowchart representative of additional alternative example machine readable instructions for implementing the example system for measuring dye concentration in liquids of FIG. 1. In the examples of FIGS. 2 and 3, as the concentration of the dye in the marked liquid 102 increases, the dye's absorption of the luminescence emitted by the luminophor on the screen 106 increases, and the luminescence detected by the photo element 108 decreases. Therefore, for large dye concentrations, the luminescence detected by the example photo element 108 can be quite small and difficult to measure. The example of FIG. 4 solves this problem by presenting a method whereby the luminescence detected by the photo element 108 increases with increasing dye concentration in the marked liquid 102.

FIG. 4 begins when the example control 110 triggers the example EM source 104 to emit light with wavelength L9 through the example tube 100 and through the example marked liquid 102 (block 400). In the example of FIG. 4, the light with wavelength L9 causes luminescence by the dye in the marked liquid 102 but does not cause luminescence by the luminophor on the screen 106. The luminescence of the dye in the example marked liquid 102 causes the dye to emit light with peak wavelength L10. This emission of light with wavelength L10 causes the luminophor on the example screen 106 to luminesce and emit light with wavelength L11. The luminescence emitted by the luminophor on the example screen 106 with wavelength L11 is not absorbed by the dye in the example marked liquid 102.

After the example control 110 triggers the EM source 104 (block 400), the control 110 turns off the EM source 104 (block 402) a short time later (e.g., 5 milliseconds). The example control 110 keeps the example EM source 104 emitting light with wavelength L9 long enough for the dye in the example marked liquid 102 to luminesce with enough strength to cause the luminophor on the example screen 106 to luminesce with a significantly strong signal to be detected by the example photo element 108. After the example control 110 turns off the example EM source 104 (block 402), the luminescence of both the dye in the example marked liquid 102 and the luminophor on the example screen 106 begin to decrease. However, these luminescent emissions do not end immediately after the example EM source 104 is turned off. Instead, the luminescent emissions continue for a short period of time after the example EM source 104 is turned off (i.e., there is an afterglow). In the example of FIG. 4, the afterglow of the dye in the marked liquid 102 lasts about 3-15 nanoseconds. However, the afterglow of the ceramic luminophor on the example screen 106 lasts about 50-150 microseconds.

After the example control 110 turns off the example EM source 104 (block 402), the control 110 measures the signal detected by the example photo element 108 after a short pause (block 404). The pause between when the example control 110 turns off the example EM source 104 (block 402) and when the control 110 measures the signal detected by the example photo element 108 (block 404) is long enough for the afterglow of the luminescence of the dye in the example marked liquid 102 to significantly decay but short enough that the afterglow of the luminescence by the luminophor on the screen 106 is still detectable by the example photo element 108 (e.g., 25 microseconds). Because of this pause, when the example control 110 measures the signal detected by the example photo element 108 (block 404), the only signal measured by the photo element 108 is the luminescence of the luminophor on the screen 106.

After the example control 110 measures the signal detected by the example photo element 108 (block 404), the control 110 determines the dye concentration in the example marked liquid 102 (block 406). Because the luminescence of the luminophor on the example screen 106 was triggered by the luminescence of the dye in the example marked liquid 102, the stronger the dye concentration in the example marked liquid 102 is, the stronger the luminescent signal detected by the example photo element 108 will be. Therefore, after an appropriate calibration, the example control 110 can determine the dye concentration in the example marked liquid 102 from the signal detected by the example photo element 108. For example, a calibration may be performed by measuring the luminescence detected by the example photo element 108 when there is no dye in the example marked liquid 102 and when a dye is diluted in the marked liquid 102 to a known concentration. After the example control 110 determines the dye concentration in the example marked liquid 108 (block 406), the example of FIG. 4 ends.

FIG. 5 is a block diagram of a processor platform 500 capable of executing the instructions of FIGS. 2-4 to implement the example system for measuring dye concentration in liquids of FIG. 1. The processor platform 500 can be, for example, a server, a personal computer, an Internet appliance, a DVD player, a CD player, a Blu-ray player, a gaming console, a personal video recorder, a smart phone, a tablet, a printer, or any other type of computing device.

The processor platform 500 of the instant example includes a processor 512. As used herein, the term "processor" refers to a logic circuit capable of executing machine readable instructions. For example, the processor 512 can be implemented by one or more microprocessors or controllers from any desired family or manufacturer.

The processor 512 includes a local memory 513 (e.g., a cache) and is in communication with a main memory including a volatile memory 514 and a non-volatile memory 516 via a bus 518. The volatile memory 514 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 416 may be implemented by flash memory and/or any other desired type of memory device. Access to the main memory 514, 516 is controlled by a memory controller.

The processor platform 500 also includes an interface circuit 520. The interface circuit 520 may be implemented by any type of interface standard, such as an Ethernet interface, a universal serial bus (USB), and/or a PCI express interface.

One or more input devices 522 are connected to the interface circuit 520. The input device(s) 522 permit a user to enter data and commands into the processor 512. The input device(s) can be implemented by, for example, a keyboard, a mouse, a touchscreen, a track-pad, a trackball, isopoint and/or a voice recognition system.

One or more output devices 524 are also connected to the interface circuit 520. The output devices 524 can be implemented, for example, by display devices (e.g., a liquid crystal display, a cathode ray tube display (CRT), a printer and/or speakers). The interface circuit 520, thus, typically includes a graphics driver card.

The interface circuit 520 also includes a communication device such as a modem or network interface card to facilitate exchange of data with external computers via a network 526 (e.g., an Ethernet connection, a digital subscriber line (DSL), a telephone line, coaxial cable, a cellular telephone system, etc.).

The processor platform 500 also includes one or more mass storage devices 528 for storing software and data. Examples of such mass storage devices 528 include floppy disk drives, hard drive disks, compact disk drives and digital versatile disk (DVD) drives.

The coded instructions 532 of FIG. 5 may be stored in the mass storage device 528, in the volatile memory 514, in the non-volatile memory 516, and/or on a removable storage medium such as a CD or DVD.

Although certain example apparatus, methods, and articles of manufacture have been disclosed herein, the scope of coverage of this patent is not limited thereto. On the contrary, this patent covers all apparatus, methods, and articles of manufacture fairly falling within the scope of the claims of this patent.

What is claimed is:

1. A method comprising:
    emitting first electromagnetic radiation having a first wavelength through a first end of a tube for a first duration of time, the tube being filled with a liquid and a dye diluted in the liquid to a first concentration;
    ceasing the emission of the first electromagnetic radiation for a second duration of time following the first duration of time;
    detecting a first strength of second electromagnetic radiation emitted by a luminophor coated on a screen at a second end of the tube at the conclusion of the second duration of time, the luminophor having luminescent properties such that the first electromagnetic radiation causes the luminophor to emit the second electromagnetic radiation having a second wavelength, wherein the second electromagnetic radiation is partially absorbed by the dye and the amount of the second electromagnetic radiation absorbed by the dye depends on the first concentration; and
    determining the first concentration based on the first strength.

2. The method of claim 1, wherein the liquid is a fuel.

3. The method of claim 1, wherein the liquid is a pharmaceutical.

4. The method of claim 1, wherein the liquid is a beverage.

5. The method of claim 1, wherein the dye is organic.

6. The method of claim 1, wherein the first end of the tube and the second end of the tube are transparent with respect to the first wavelength and the second wavelength.

7. The method of claim 1, wherein the first electromagnetic radiation is visible light.

8. The method of claim 1, wherein the first electromagnetic radiation is infrared light.

9. The method of claim 1, wherein the first electromagnetic radiation is ultraviolet light.

10. The method of claim 1, further comprising performing a calibration by detecting the first strength when the first concentration is a known concentration.

11. The method of claim 1, wherein the dye is invisible to the naked eye.

12. The method of claim 1, wherein the dye is visible to the naked eye.

13. A method comprising:

emitting first electromagnetic radiation having a first wavelength through a first end of a tube for a first duration of time, the tube being filled with a liquid and a dye diluted in the liquid to a first concentration;

ceasing the emission of the first electromagnetic radiation for a second duration of time following the first duration of time;

detecting a first strength of second electromagnetic radiation emitted by a luminophor coated on a screen at a second end of the tube at the conclusion of the second duration of time, the luminophor having luminescent properties such that the first electromagnetic radiation causes the luminophor to emit the second electromagnetic radiation having a second wavelength, wherein the second electromagnetic radiation is partially absorbed by the dye and the amount of the second electromagnetic radiation absorbed by the dye depends on the first concentration;

emitting third electromagnetic radiation having a third wavelength through the first end of the tube for a third duration of time after detecting the first strength;

ceasing the emission of the third electromagnetic radiation for a fourth duration of time following the third duration of time detecting a second strength of fourth electromagnetic radiation emitted by the luminophor at the conclusion of the fourth duration of time, the luminophor having luminescent properties such that the third electromagnetic radiation causes the luminophor to emit the fourth electromagnetic radiation having a fourth wavelength, wherein the fourth electromagnetic radiation is not absorbed by the dye; and determining the first concentration based on a ratio between the first strength and the second strength.

14. The method of claim 13, further comprising performing a calibration by detecting the first strength and the second strength when the first concentration is a known concentration.

15. The method of claim 13, wherein the dye is organic.

16. The method of claim 13, wherein the first electromagnetic radiation is visible light.

17. The method of claim 1, wherein the first electromagnetic radiation is infrared light.

18. The method of claim 1, wherein the first electromagnetic radiation is ultraviolet light.

19. A method comprising:

emitting first electromagnetic radiation having a first wavelength through a first end of a tube for a first duration of time, the tube being filled with a liquid and a dye diluted in the liquid to a first concentration, the dye having luminescent properties such that the first electromagnetic radiation causes the dye to emit second electromagnetic radiation having a second wavelength;

ceasing the emission of the first electromagnetic radiation for a second duration of time following the first duration of time;

detecting a first strength of third electromagnetic radiation emitted by a luminophor coated on a screen at a second end of the tube at the conclusion of the second duration of time, the luminophor having luminescent properties such that the second electromagnetic radiation causes the luminophor to emit the third electromagnetic radiation having a third wavelength, wherein the third electromagnetic radiation is not absorbed by the dye; and determining the first concentration based on the first strength.

20. The method of claim 15, further comprising performing a calibration by detecting the first strength when the first concentration is a known concentration.

* * * * *